(12) United States Patent
Rios et al.

(10) Patent No.: US 8,455,460 B2
(45) Date of Patent: Jun. 4, 2013

(54) COSMETIC COMPOSITION CONTAINING ONE OR MORE COMPOUNDS OF THE β-(1,3)-GLUCURONAN OR β-(1,3)-GLUCOGLUCURONAN TYPE

(75) Inventors: Laurent Rios, Azuat la Combelle (FR); Cédric Delattre, Beaumont (FR); Céline Laroche, Crevant-Laveine (FR); Philippe Michaud, Billon (FR); Jean-Yves Berthon, Romagnat (FR)

(73) Assignees: Greentech, St. Beauzire (FR); Universite Blaise Pascal, Clermont Ferrand (FR)

( * ) Notice: Subject to any disclaimer, the term of this patent is extended or adjusted under 35 U.S.C. 154(b) by 427 days.

(21) Appl. No.: 12/674,698

(22) PCT Filed: Aug. 28, 2008

(86) PCT No.: PCT/FR2008/001211
§ 371 (c)(1),
(2), (4) Date: Jun. 7, 2010

(87) PCT Pub. No.: WO2009/060140
PCT Pub. Date: May 14, 2009

(65) Prior Publication Data
US 2011/0124854 A1    May 26, 2011

(30) Foreign Application Priority Data

Aug. 31, 2007   (FR) ..................................... 07 06121
May 27, 2008   (FR) ..................................... 08 02869

(51) Int. Cl.
*A61K 31/715*   (2006.01)
*A61K 31/716*   (2006.01)
*A61Q 19/00*   (2006.01)
*A61Q 5/00*   (2006.01)

(52) U.S. Cl.
USPC .............................................. 514/54; 514/844

(58) Field of Classification Search
USPC ...................................................... 514/54, 844
See application file for complete search history.

(56) References Cited

U.S. PATENT DOCUMENTS

2003/0209336 A1   11/2003   Cimecioglu et al.
2004/0260082 A1 *   12/2004   Van Der Wilden et al. ......................... 536/123.12

FOREIGN PATENT DOCUMENTS

| WO | 9104988 A1 | 4/1991 |
| WO | 9507303 A1 | 3/1995 |
| WO | 2005115326 A1 | 12/2005 |

OTHER PUBLICATIONS

Karkkainen ("Structural analysis of trisaccharides as permethylated methyl glycosides by gas-liquid chromatography-mass spectrometry", Carbohydrate Research, (1971), vol. 17, No. 1, pp. 1-10).*

* cited by examiner

*Primary Examiner* — Patrick T. Lewis
*Assistant Examiner* — Everett White
(74) *Attorney, Agent, or Firm* — Porzio, Bromberg & Newman, P.C.

(57) ABSTRACT

The invention relates to a cosmetic composition that contains one or more compounds of the β-(1,3)-glucuronane or β-(1, 3)-glucoglucuronane type as well as the pharmaceutically acceptable salt thereof, and to the use of this composition and these compounds for various cosmetic applications.

7 Claims, No Drawings

COSMETIC COMPOSITION CONTAINING ONE OR MORE COMPOUNDS OF THE β-(1,3)-GLUCURONAN OR β-(1,3)-GLUCOGLUCURONAN TYPE

CROSS REFERENCE TO RELATED APPLICATION

This is a National Stage of International Application No. PCT/FR2008/001211, filed Aug. 28, 2008, which claims the benefit of Application No. 0706121, filed in France on Aug. 31, 2007 and Application No. 0802869 filed in France on May 27, 2008, the disclosures of which Applications are incorporated by reference herein.

The present invention relates to a cosmetic composition comprising one or more compounds of the β-(1,3)-glucuronan or β-(1,3)-glucoglucuronan type as well as their pharmaceutically acceptable salt, and the use of said composition and of said compounds for various cosmetic applications.

The glucuronans are natural polysaccharides or chemically oxidized natural polysaccharides, containing significant proportions of segments of glucuronic acids joined by bonds of type β-(1,3), β-(1,4), α-(1,3) or α-(1,4). As examples, we may mention the bacterial and fungal glucuronans (Dantas L. et al., *Carbohydr. Res.* 1994, 265, 303-310; De Ruiter G. A. et al., *Carbohyd. Pol.* 1992, 18, 1-7; Park J. K. et al., *Carbohyd. Pol.* 2006, 63, 482-486).

Earlier studies showed that polyglucuronic acids could be obtained by so-called regioselective chemical oxidation routes from natural polysaccharides. Notably, the oxidation of polysaccharides by nitrogen dioxide ($NO_2/N_2O_4$), as oxidizing agent, is a reaction that is often used. Thus, Vignon et al., in French patent application FR A 2 873 700, described an oxidation reaction of cellulose in an inert gas in the supercritical state using nitrogen dioxide as oxidizing agent. The polyglucuronic acids obtained by this method have a proportion of carboxylic acid as percentage by weight of up to 25.5% in the case of cellulose. However, methods of this type have the usual drawbacks when handling gases under pressure. Moreover, it has been shown that the use of the TEMPO reagent in a sodium hypochloride medium also made possible the regioselective oxidation of the primary alcohol functions of certain monosaccharides (N. J. Davis and S. L. Flitsch, *Tetrahedron Letters* 1993, 34(7), 1181-1184). Using a similar method, Vignon et al., in international patent application WO 03/035699, describe the oxidation, using the TEMPO reagent, of esterified polyanhydroglucoses and more particularly of cellulose esters. The method described by Vignon necessitates working with water-soluble or water-dispersible esterified celluloses. The products obtained by this method have numerous applications.

Thus, patent application WO 91/04988 describes the use of such compounds as complexing agent, additive, carrier, stabilizer or solubilizer, whereas patent application US 2003/0209336 describes the use of said compounds as additives for paper.

These compounds have never been used or described as having any activity in the cosmetic field.

It has now been discovered, quite surprisingly, that these compounds can be used for the preparation of cosmetic compositions having very varied activities. Thus, it was demonstrated for example within the scope of the present invention that cosmetic compositions comprising, as active principle, one or more β-(1,3)-glucuronans or β-(1,3)-glucoglucuronans, have various and varied properties, such as reducing, anticellulite, firming, hydrating, antimicrobial, antioxidant, antiradical, wound-healing, lifting, antiwrinkle, chelating, complexing and sequestering, soothing, concealing, anti-redness, and emollient properties, hair disentangling properties, antidandruff properties, hair restoring properties, hair coating properties, epilatory properties, properties of limiting the regrowth of facial and body hair, properties of participating in cellular renewal, modulating the inflammatory response or participating in maintaining the oval shape of the face.

The present invention therefore relates to a cosmetic composition comprising, as active principle, one or more β-(1,3)-glucuronans or β-(1,3)-glucoglucuronans of formula (I):

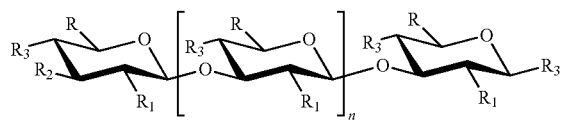

in which:
R$_1$, R$_2$ and R$_3$, which may be identical or different, selected independently for each glucose unit, represent a hydroxyl, alkoxy, acyloxy or sulfonyloxy group;
R, selected independently for each glucose unit, represents a carboxyl, alkoxycarbonyl, acyl group, or a group —CH$_2$R$_4$, where R$_4$ represents a hydroxyl, alkoxy, acyloxy, sulfonyloxy, sulfinyl group;
n is selected in such a way that the average molecular weights are between 500 and 4 000 000 dalton;
and where at least 0.1% of the groups R, selected independently for each of the glucose units in question, represent a carboxyl, alkoxycarbonyl, acyl group; as well as their pharmaceutically acceptable salt.

Within the scope of the present invention:
the expressions "degree of oxidation" and "molecular weight" used hereinafter refer indiscriminately to the molecule alone or to the mixture of molecules and then represent in this case an average value;
the expression "degree of oxidation of β-(1,3)-glucuronans and/or β-(1,3)-glucoglucuronans" used hereinafter denotes the percentage of glucuronic units or of units derived from glucuronic acid present in the sequence of units of said β-(1,3)-glucuronans and/or β-(1,3)-glucoglucuronans. More precisely, said degree of oxidation according to the present invention is characterized by the percentage of groups representing a carboxyl, alkoxycarbonyl or acyl group, relative to all of the groups R;
"alkyl group" means a saturated, monovalent, linear or branched hydrocarbon chain, having from 1 to 6 carbon atoms, representative elements of which are for example the following: the methyl, ethyl, n-propyl, iso-propyl, n-butyl, sec-butyl, iso-butyl, tert-butyl, pentyl, hexyl groups;
the term "alkyl" as defined above keeps the same definition when it incorporates the name of a group, for example in the alkoxy group. Thus, among the alkoxy groups, representative elements are as follows: the methoxy, ethoxy, n-propoxy, iso-propoxy, n-butoxy, iso-butoxy, sec-butoxy, tert-butoxy, pentyloxy groups;
"pharmaceutically acceptable salt" means any salt of addition with a mineral or organic acid by the action of said acid within an organic or aqueous solvent such as an alcohol, a ketone, an ether or a chlorinated solvent, and which is acceptable from the pharmaceutical standpoint. As examples of said salts, we may mention the following salts: benzenesulfonate, hydrobromide, hydrochloride, citrate, ethanesulfonate, fumarate, gluconate, iodate, isethionate, maleate, methanesulfonate, methylene-bis-b-oxynaphthoate, nitrate, oxalate, palmoate, phosphate, salicylate, sulfate, tartrate, theophyllinacetate and p-toluenesulfonate.

Preferably, the present invention relates to a cosmetic composition comprising, as active principle, one or more β-(1,3)-glucuronans or β-(1,3)-glucoglucuronans of formula (I) as defined above, and in which the following characteristics are selected alone, or in combination:
  $R_1$, $R_2$ and $R_3$, which may be identical or different, are selected independently for each glucose unit, and represent a hydroxyl, alkoxy, or sulfonyloxy group, preferably a hydroxyl or alkoxy group;
  R, selected independently for each glucose unit, represents a carboxyl or acyl group, or a group —$CH_2R_4$, where $R_4$ represents a hydroxyl, alkoxy, or sulfonyloxy group, preferably a hydroxyl or alkoxy group;
  n is selected in such a way that the average molecular weights are between 500 and 4 000 000 dalton, preferably from 500 to 200 000 dalton, even more preferably less than 5000 dalton and the degrees of polymerization of said oligo- and/or polysaccharides are of the order of 25;
  the compounds of formula (I) have a degree of oxidation of at least 5%, preferably of at least 30%, more preferably of at least 90%. Quite preferably, the compounds of formula (I) are 100% oxidized.

Even more preferably, the present invention relates to a cosmetic composition comprising one or more β-(1,3)-glucuronans or β-(1,3)-glucoglucuronans of formula (I) as defined above, and in which the groups $R_1$, $R_2$ and $R_3$ represent a hydroxyl group and the groups R represent a carboxyl group or a group —$CH_2OH$. Even more preferably, the present invention relates to a cosmetic composition comprising one or more β-(1,3)-glucuronans or β-(1,3)-glucoglucuronans of formula (I) as defined above, and in which the groups $R_1$, $R_2$ and $R_3$ represent a hydroxyl group and the groups R represent a carboxyl group or a group —$CH_2OH$, said compounds having a degree of oxidation of at least 95%.

The present invention relates more particularly to a cosmetic composition comprising, as active principle, one or more β-(1,3)-glucuronans of formula (II):

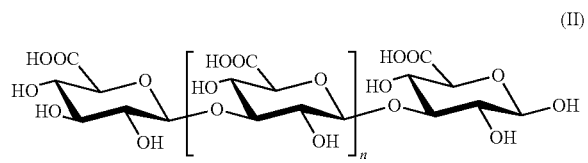

in which n is selected in such a way that the average molecular weights are between 500 and 2 500 000 dalton.

Preferably, the present invention relates to a cosmetic composition comprising, as active principle, one or more β-(1,3)-glucuronans of formula (II) as defined above, and in which n is selected in such a way that the average molecular weights are between 500 and 200 000 dalton, preferably between 500 and 5000 dalton.

Quite preferably, the present invention relates to a cosmetic composition comprising, as active principle, one or more β-(1,3)-glucuronans or β-(1,3)-glucoglucuronans possessing various degrees of oxidation, linear and non-branched, selected from:

β-(1,3)-D-polyglucuronic acid having molecular weights between 500 and 2 500 000 dalton;
peracetylated β-(1,3)-D-polyglucuronic acid having molecular weights between 600 and 3 500 000 dalton; and
β-(1,3)-D-polyglucuronic acid, sulfated in positions C2 and C4 and having molecular weights between 800 and 4 000 000 dalton.

The compounds of the β-(1,3)-glucuronan and/or β-(1,3)-glucoglucuronan type as defined previously can be prepared according to methods well known by a person skilled in the art. As examples of said methods, we may mention the method of preparation from at least one linear, non-branched and non-esterified β-(1,3)-glucan, comprising at least one operation of regioselective oxidation in position C6 of said β-(1,3)-glucans by means of 2,2,6,6-tetramethylpiperidine-1-oxyl (TEMPO) and of at least one alkali metal hypochlorite as co-additive.

Preferably, said stage of regioselective oxidation in the method according to the present invention is carried out using 2,2,6,6-tetramethylpiperidine-1-oxyl (TEMPO), and using an alkali metal hypochlorite co-additive together with an alkali metal bromide. More preferably, the alkali metal hypochlorite co-additive is sodium hypochlorite and the alkali metal bromide is sodium bromide.

Said linear, non-branched and non-esterified β-(1,3)-glucan used for carrying out the method according to the invention will be designated as "substrate" hereinafter.

Said substrate can be a linear, non-branched and non-esterified β-(1,3)-glucan obtained by synthesis or hemisynthesis, or can be of natural origin, preferably bacterial origin. Said substrate can have a molar mass by weight of the order of 500 to 2 500 000 dalton.

Preferably, said substrate is selected from the linear, non-branched and non-esterified β-(1,3)-glucans, water-soluble (solubility of at least 1 g/l in water of alkaline pH) or not forming an aggregate over time.

A preferred substrate is curdlan, a linear, non-branched β-(1,3)-glucan with a molecular size of about 2 000 000 to 2 500 000 dalton, which is produced notably by bacteria of the genera *Agrobacterium* and *Rhizobium*.

The selective oxidation stage is generally carried out according to the method described in patent application FR A 2 831 171.

Different degrees of oxidation of the β-(1,3)-glucoglucuronans prepared by said method can be obtained by controlling, for example, the reaction time in said selective oxidation stage. In particular, complete oxidation of the substrate can be obtained. Thus, said reaction of selective oxidation can be stopped, for example, by adding a mineral acid such as hydrochloric or sulfuric acid. The β-(1,3)-glucuronans and/or β-(1,3)-glucoglucuronans can optionally be precipitated by means of an alcohol such as ethanol. The β-(1,3)-glucuronans and/or β-(1,3)-glucoglucuronans obtained at the end of the oxidation stage can optionally be purified by any known usual method, for example redissolving, washing, dialysis, or tangential-flow nanofiltration and ultrafiltration.

Thus, a preferred method is that which makes it possible to obtain β-(1,3)-glucoglucuronans having at least 95% of the groups R constituted of a carboxyl group or β-(1,3)-glucuronans.

In order to modulate the properties of the β-(1,3)-glucuronans and/or β-(1,3)-glucoglucuronans obtained, said selective oxidation stage of said method can be followed by the following two stages, in any order:
a) an operation of chemical functionalization with functions selected from: methyl, methyloxy, ethyl, ethyloxy, butyl, butyloxy, isobutyl, isobutyloxy, propyl, propyloxy, isopropyl, isopropyloxy, sulfate, sulfoacetate, acetate, propionate, acetobutyrate, acetopropionate, glycerate or phosphoryl;

b) an operation of chemical and/or physical and/or enzymatic degradation.

Preferably, said selective oxidation stage of said method can be followed by the following two stages, in any order:

c) an operation of chemical functionalization with functions selected from: methyl, methyloxy, ethyl, ethyloxy, butyl, butyloxy, sulfate, sulfoacetate, or phosphoryl;

d) an operation of chemical and/or physical and/or enzymatic degradation.

Said stages can be carried out according to the known methods. The intermediate and/or final β-(1,3)-glucuronans and/or β-(1,3)-glucoglucuronans obtained at the end of either of the stages or of the two stages of said method can optionally be purified by any usual known method, for example redissolving, washing, removal of salts by dialysis, tangential-flow nano- or ultrafiltration.

The β-(1,3)-glucuronans and/or β-(1,3)-glucoglucuronans represented by formulas (I) or (II) or the intermediates obtained by the method of the present invention can be purified by the usual known methods, for example by redissolving, washing, dialysis or tangential-flow nano- or ultrafiltration.

The compositions according to the present invention can be formulated in a pharmaceutical form: creams, gels, lotions, milks, oil-in-water or water-in-oil emulsions, solutions, ointments, sprays, body oils, hair lotions, shampoos, after-shave lotions, soaps, protective lipsticks, make-up sticks and pencils with contents from 0.01% to 75 wt. %, preferably between 0.01% and 25% in the form of powder and contents between 0.01% and 35%, preferably between 0.01% and 15% in encapsulated form.

For the preparation of these compositions, one or more compounds of the β-(1,3)-glucuronan or β-(1,3)-glucoglucuronan type or one or more of their pharmaceutically acceptable salts are mixed with the excipients generally used in the cosmetics industry.

The compositions according to the present invention can be in the form of a cream in which one or more compounds of the β-(1,3)-glucuronan or β-(1,3)-glucoglucuronan type or one or more of their pharmaceutically acceptable salts are combined with the excipients commonly used in cosmetology.

The compositions according to the present invention can be in the form of gels in the appropriate excipients, such as cellulose esters or other gelling agents, such as carbopol, guar gum, etc.

The compositions according to the present invention can also be in the form of a lotion or of a solution in which one or more compounds of the β-(1,3)-glucuronan or β-(1,3)-glucoglucuronan type or one or more of their pharmaceutically acceptable salts are in encapsulated form.

The microspheres according to the invention can for example be constituted of fats, agar and water. One or more compounds of the β-(1,3)-glucuronan or β-(1,3)-glucoglucuronan type or one or more of their pharmaceutically acceptable salts can be incorporated in carriers such as liposomes, glycospheres, cyclodextrins, in chylomicrons, macro-, micro-, nano-particles as well as macro-, micro- and nano-capsules and can also be absorbed on powdered organic polymers, talcs, bentonites and other mineral substrates.

These emulsions have good stability and can be stored for the time necessary for use at temperatures between 0° C. and 50° C. without sedimentation of the constituents or separation of the phases.

The compositions according to the present invention can also contain additives or adjuvants that are usual in cosmetology, for example antimicrobial agents or perfumes but also extracted or synthetic lipids, gelling and viscosity-enhancing polymers, surfactants and emulsifiers, water-soluble or fat-soluble active principles, plant extracts, tissue extracts, marine extracts, synthetic actives.

The compositions according to the present invention can also comprise other additional active principles selected for their action, for example for the reducing effect, anticellulite effect, firming effect, hydrating effect, antimicrobial activity, antioxidant activity, antiradical activity, the wound-healing effect, lifting effect, antiwrinkle effect, chelating activity, complexing and sequestering activity, the soothing effect, concealing effect, anti-redness effect, emollient activity, hair disentangling effect, antidandruff activity, the hair restoring effect, hair coating effect, epilatory activity, activity limiting the regrowth of facial and body hair, the activity of participating in cellular renewal, the activity of modulating the inflammatory response, the activity of participating in maintaining the oval shape of the face, but also sun protection, anti-irritant activity, cellular nutrition, cellular respiration, antiseborrheic treatments, skin tonicity, protection of the hair.

When the compositions according to the present invention contain additional active principles, the latter are generally present in the composition at a concentration that is high enough for them to exert their activity.

The compositions according to the present invention are preferably for daily use, applying them one or more times per day.

The compositions according to the present invention are very well tolerated, they do not exhibit any toxicity and their application on the skin, for prolonged periods of time, does not lead to any systematic effect.

The compositions according to the present invention can be used for numerous cosmetic applications. As examples, we may mention the use of a composition according to the present invention as reducing composition, anticellulite composition, firming composition, hydrating composition, antimicrobial composition, antioxidant composition, antiradical composition, wound-healing composition, lifting composition, antiwrinkle composition, chelating composition, complexing and sequestering composition, soothing composition, concealing composition, anti-redness composition, emollient composition, hair disentangling composition, antidandruff composition, hair restoring composition, hair coating composition, epilatory composition, composition limiting the regrowth of facial and body hair, composition participating in cellular renewal, composition modulating the inflammatory response, and composition participating in maintaining the oval shape of the face. Preferably, the composition according to the present invention is used as reducing composition, anticellulite composition, firming composition, wound-healing composition, antiwrinkle composition, concealing composition or antiinflammatory composition. Quite preferably, the composition according to the present invention is used as a reducing composition.

It has in fact been discovered that the β-(1,3)-glucuronan or β-(1,3)-glucoglucuronan compounds of formula (I) as defined according to the present invention induce the production and organization of fibrils of collagen responsible for the reorganization of the extracellular matrix combined with modulation of the immune response. On this basis these compounds can be used for cellular renewal, for modulation of inflammation, as soothing agents and as hydrating agents.

It has also been discovered that the β-(1,3)-glucuronan or β-(1,3)-glucoglucuronan compounds of formula (I) as defined according to the present invention display reducing cosmetic properties when they are applied topically or systemically. In fact, these compounds lead to overexpression of the ANGPTL4 gene that codes for the adipokine which notably possesses the property of inhibiting the activity of the enzyme lipoprotein lipase (LPL), which is fixed on the vascular endothelium attached to the adipose tissues. The enzymatic inhibition prevents the transfer of fatty acids from the lipoproteins to the adipocytes, thus greatly reducing lipogenesis. Moreover, the adipokine possesses the property of activating the enzyme ATGL (adipose triglyceride lipase), present in the adipocytes. This enzymatic activation thus greatly increases lipolysis and the release of fatty acids from the adipocytes.

Thus, another object of the present invention relates to the use of one or more β-(1,3)-glucuronans or β-(1,3)-glucoglucuronans of formula (I) as defined according to the present invention as reducing agent, as anticellulite agent, as firming agent, as hydrating agent, as antimicrobial agent, as antioxidant agent, as antiradical agent, as wound-healing agent, as lifting agent, as antiwrinkle agent, as chelating agent, as complexing and sequestering agent, as soothing agent, as concealing agent, as anti-redness agent, as emollient agent, as hair disentangling agent, as antidandruff agent, as hair restoring agent, as hair coating agent, as epilatory agent, as agent limiting the regrowth of facial and body hair, as agent participating in cellular renewal, as agent modulating the inflammatory response or as agent participating in maintaining the oval shape of the face. Preferably, the β-(1,3)-glucuronans or β-(1,3)-glucoglucuronans of formula (I) as defined according to the present invention are used as reducing agent, as anticellulite agent, as firming agent, as wound-healing agent, as antiwrinkle agent, as concealing agent, or as antiinflammatory agent. Quite preferably, the β-(1,3)-glucuronans or β-(1,3)-glucoglucuronans of formula (I) as defined according to the present invention are used as reducing agent.

The present invention is illustrated by but is not limited to the following examples.

EXAMPLE 1

Example of Preparation of β-(1,3)-Glucuronan or β-(1,3)-Glucoglucuronan Compounds The $^{13}$C NMR spectra were recorded on an Avance 400 Bruker NMR spectrometer (9.4 T, 400 MHz). 30000 accumulations were performed at 30° C.

Production of β-(1,3)-Glucuronan in Liquid Medium (Degree of Oxidation of at Least 95%).

Curdlan (10 g) is dissolved in distilled water (1 L) at a temperature of 0° C. and at pH 10. TEMPO (43.3 mg), NaBr (0.95 g) and NaClO (50 mL at 13%) are added to the reaction mixture. The oxidation reaction is stopped after 1 hour by adding methanol, then neutralized with hydrochloric acid (2M). The β-(1,3)-glucuronan formed is precipitated with iced alcohol. This anionic polysaccharide is then recovered by centrifugation (15000 g, 20 min, 4° C.) and then finally dried by lyophilization (24 h).

$^{13}$C NMR analysis reveals complete oxidation of the C6 carbon of the curdlan since a signal at 61.4 ppm corresponding to the C6 carbon bearing the primary alcohol (CH$_2$OH) has completely disappeared and a new signal at 175.5 ppm appears, which is characteristic of carboxylation of the C6 carbon of curdlan (COO$^-$). The degree of oxidation is also calculated by conductometric determination.

Production of β-(1,3)-Glucoglucuronan in Liquid Medium (41% Oxidation)

Curdlan (10 g) is dissolved in distilled water (1 L) at a temperature of 0° C. and at pH 10. TEMPO (43.3 mg), NaBr (0.95 g) and NaClO (50 mL at 13%) are added to the reaction mixture. The oxidation reaction is stopped after 30 minutes by adding methanol, then neutralized with hydrochloric acid (2M). The β-(1,3)-glucoglucuronan formed is precipitated with iced alcohol. This partially oxidized polysaccharide is then recovered by centrifugation (15000 g, 20 min, 4° C.) and then finally dried by lyophilization (24 h).

$^{13}$C NMR analysis reveals partial oxidation (41%) of the C6 carbon of the curdlan by integration of the signals at 175.5 ppm and 61.4 ppm.

Thermal Degradation of β-(1,3)-Glucuronan

A solution of β-(1,3)-glucuronan (10 g/L in the water) is heated at a temperature of 100° C. for 20 minutes. After cooling, the solution is acidified (pH 2) and then centrifuged (15000 g, 20 min, 4° C.). The supernatant containing the oligosaccharides is recovered, neutralized and then dried by lyophilization.

Peracetylation of β-(1,3)-Glucuronan

A solution of β-(1,3)-glucuronan (10 g/L in pyridine), to which acetic anhydride is added (1 volume), is held at room temperature for a period of at least 24 hours (24-48 hours) and then evaporated under vacuum. The peracetylated β-(1,3)-glucuronan thus obtained is recovered.

$^{13}$C NMR analysis of these molecules reveals the presence of a signal at 23.4 ppm, characteristic of the methyl group of the acetate, thus confirming the acetylation of the β-(1,3)-polyglucuronic acid.

Persulfation of β-(1,3)-Glucuronan

A solution of β-(1,3)-glucuronan (10 g/L in DMF), to which a solution of SO$_3$/DMF is added (1 volume), is held at room temperature for a period of at least 24 hours (24 to 48 hours) and then neutralized before being lyophilized. The degree of sulfation is measured by potentiometric determination.

EXAMPLE 2

Cosmetic Activities of β-(1,3)-Glucuronan and β-(1,3)-Glucoglucuronan Compounds

The biological activities of β-(1,3)-glucuronan compounds or of a mixture of β-(1,3)-glucoglucuronan compounds were screened by an original method of molecular biology (transcriptomic technique) and then detected by methodologies used conventionally in cosmetology.

Example 2.1

Reducing, Anticellulite, Anti-Orange-Peel Skin Effect Activities of a β-(1,3)-Glucuronan Compound or of a Mixture of β-(1,3)-Glucoglucuronan Compounds A transcriptomic study carried out on human fibroblasts cultivated in vitro in the absence or in the presence of one or more of these compounds showed that these molecules lead to overexpression of the ANGPTL4 gene that codes for the adipokine of the same name. This adipokine produced locally in the adipose tissue inhibits the activity of the enzyme lipoprotein lipase (LPL) thus preventing the transfer of fatty acids from the lipoproteins to the adipocytes, thus greatly reducing lipogenesis. At the same time, this adipokine activates the enzyme ATGL (adipose triglyceride lipase), present in the adipocytes, thus greatly increasing lipolysis and the release of fatty acids from the adipocytes.

These results were supplemented with an in-vitro study, conducted on adipocytes cultivated in the absence or in the presence of a β-(1,3)-glucuronan compound or a mixture of β-(1,3)-glucoglucuronan compounds, at a concentration of 0.5%, which was able showed that these molecules induce a decrease of the order of 25% in the density of fatty acids stored in the form of triglycerides in the lipid vacuoles of the adipocytes. Moreover, a second in-vitro study, conducted on pre-adipocytes, showed that the use of one or more of these compounds (at a concentration of 0.5%) greatly reduces the differentiation of the pre-adipocytes into mature adipocytes (decrease in expression of the marker aP2/FABP4).

The decrease in lipogenesis, increase in lipolysis, increase in release of fatty acids from the adipocytes, increase in the utilization of these fatty acids and the decrease in differentiation of the pre-adipocytes to mature adipocytes induced by the β-(1,3)-glucuronan compound or the mixture of β-(1,3)-glucoglucuronan compounds provide evidence of the reducing activity of these molecules.

A clinical study, conducted on human volunteers, showed that the daily topical application, for 30 days, of a cosmetic preparation in the form of cream containing 3% of a β-(1,3)-glucuronan compound or 3% of a mixture of β-(1,3)-glucoglucuronan compounds, leads to a significant decrease in cellulite in more than 63% of these individuals. The orange-peel skin effect is reduced in 53% of the volunteers (against 27% in the group of volunteers treated with a placebo).

Example 2.2

Wound-Healing Activity and Effect on Tissue Remodelling of a β-(1,3)-Glucuronan Compound, or of a Mixture of β-(1,3)-Glucoglucuronan Compounds A transcriptomic study conducted on human fibroblasts cultivated in vitro in the absence or in the presence of one or more of these compounds showed that these molecules lead to overexpression of the genes MMP, EGR1, WNT11, PDGFD, TFPI2, PTGS2 and under-expression of the HAPLN1 gene coding for the proteins with the same names, involved in the processes of cicatrization and tissue remodelling. In fact, the transitory induction (under the control of TFPI2 and of PDGFD) of the metalloproteinases (MMP) and the transitory inhibition (under the control of TFPI2) of HAPLN1, permit transitory, localized destabilization of the stressed site (requiring cicatrization) of the extracellular matrix, mainly by catabolic action on the collagen fibers. Following degradation of the extracellular matrix, controlled by TFPI2, which permitted removal of the damaged collagen fibers and the migration and proliferation (controlled by PTGS2) of the cells that are essential to the process of tissue remodelling (fibroblasts, keratinocytes, melanocytes, etc.), the proteins EGR1 and WNT11 permit stimulation of the synthesis of collagen fibers and therefore reconstruction and stabilization of the new extracellular matrix. Therefore, through induction of expression of these proteins, the β-(1,3)-glucuronan compound or the mixture of β-(1,3)-glucoglucuronan compounds are endowed with wound-healing activity and an action on tissue remodelling that can be used in cosmetics, notably in wound-healing, anti-aging, antiwrinkle, concealing, lifting, firming, and hydrating products and those helping to maintain the oval shape of the face.

Example 2.3

Effect of a β-(1,3)-Glucuronan Compound, or of a Mixture of β-(1,3)-Glucoglucuronan Compounds on Cellular Renewal A transcriptomic study conducted on human fibroblasts cultivated in vitro in the absence or in the presence of a β-(1,3)-glucuronan compound or a mixture of β-(1,3)-glucoglucuronan compounds showed that these molecules lead to overexpression of the genes EGR1, PTGS2, PDGFD, NPTX1 coding for the proteins with the same names that are responsible for the activation, proliferation and differentiation (under the control of TFPI2, which is also overexpressed) of the fibroblasts, keratinocytes and melanocytes, which are target cells of the cosmetics.

Example 2.4

Antiinflammatory Activity of a β-(1,3)-Glucuronan Compound, or of a Mixture of β-(1,3)-Glucoglucuronan Compounds A transcriptomic study conducted on human fibroblasts cultivated in vitro in the absence or in the presence of one or more of these compounds showed that these molecules lead to overexpression of the genes NPTX1, PTGS2 and APOE coding for the proteins with the same names that are responsible for antiinflammatory activity. In fact, the protein PTGS2 performs the role of a negative regulator of inflammation by inhibiting the switch of prostaglandin E2 to prostaglandin D2 (pro-inflammatory). Moreover, APOE acts as a negative regulator of inflammation by reducing the influx of monocytes to the site of inflammation. For its part, NPTX1 inhibits activation of the T cells. Therefore, through induction of expression of these proteins, the β-(1,3)-glucuronan compound or the mixture of β-(1,3)-glucoglucuronan compounds are endowed with antiinflammatory activity that can be used in cosmetics, notably in antiinflammatory, anti-redness and/or soothing products.

Example 2.5

Antioxidant and Antiradical Activities of a β-(1,3)-Glucuronan Compound, or of a Mixture of β-(1,3)-Glucoglucuronan Compounds A transcriptomic study conducted on human fibroblasts cultivated in vitro in the absence or in the presence of one or more of these compounds showed that these molecules lead to overexpression of the genes ALDH3A1, EPXH1 and HSPA6 coding for the proteins with the same names that are responsible for antioxidant and antiradical activities. In fact, the protein ALDH3A1 is involved, simultaneously, in the direct trapping of free radicals, in maintaining the redox balance, in maintaining glutathione status (an antioxidant molecule), and in the detoxification of lipids and peroxidized aldehydes. Moreover, the protein EPXH1 takes part in the metabolism of peroxidized lipids and in the detoxification of electrophiles (styrene oxide, ethylene oxide, gamma radiation, etc.). For its part, the protein HSPA6 is active against oxidative stress in general at the cellular level. Therefore, by induction of expression of these proteins, the β-(1,3)-glucuronan compound or the mixture of β-(1,3)-glucoglucuronan compounds can be used as active principles, and/or in combination with other compounds, for the preparation of cosmetic compositions possessing antioxidant and/or antiradical activities.

Example 2.6

Chelating and Sequestering Activities of a β-(1,3)-Glucuronan Compound, or of a Mixture of β-(1,3)-Glucoglucuronan Compounds The β-(1,3)-glucuronan compounds or the mixture of β-(1,3)-glucoglucuronan compounds are polyanionic molecules capable of chelating and of sequestering mono- and divalent cationic ions. This was demonstrated by the dissolution of monovalent cationic ions (notably Na+ and Cu+) and/or divalent cationic ions (notably including Cu2+, Ca2+, Mg2+ and Zn2+), with stirring, in the presence of a β-(1,3)-glucuronan compound or a mixture of β-(1,3)-glucoglucuronan compounds. After the compounds were recovered and washed, investigation by atomic absorption showed that the β-(1,3)-glucuronan compound or the mixture of β-(1,3)-glucoglucuronan compounds chelate and sequester mono- and divalent cationic ions.

The invention claimed is:

1. A cosmetic composition comprising, as active principle, one or more β-(1,3)-glucuronans or β-(1,3)-glucoglucuronans of formula (I):

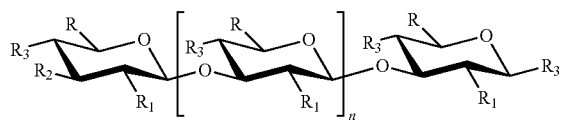

(I)

in which:
R₁, R₂ and R₃, which may be identical or different, selected independently for each glucose unit, represent a hydroxyl, alkoxy, acyloxy or sulfonyloxy group;
R, selected independently for each glucose unit, represents a carboxyl, alkoxycarbonyl, acyl group, or a group —CH₂R₄, where R₄ represents a hydroxyl, alkoxy, acyloxy, sulfonyloxy, or sulfinyl group;
n is selected in such a way that the average molecular weights are between 500 and 4 000 000 dalton;
and where at least 0.1% of the groups R, selected independently for each of the glucose units in question, represent a carboxyl, alkoxycarbonyl, or acyl group; as well as their pharmaceutically acceptable salt.

2. The composition as claimed in claim 1, wherein R₁, R₂ and R₃, which may be identical or different, are selected independently for each glucose unit, and represent a hydroxyl, alkoxy, or sulfonyloxy group.

3. The composition as claimed in claim 1, wherein R, selected independently for each glucose unit, represents a carboxyl or acyl group, or a group —CH₂R₄, where R₄ represents a hydroxyl, alkoxy, or sulfonyloxy group.

4. The composition as claimed in claim 1, wherein n is selected in such a way that the average molecular weights are between 500 and 200 000 dalton.

5. The composition as claimed in claim 1, wherein the compounds of formula (I) have a degree of oxidation of at least 5%.

6. The composition as claimed in claim 1, wherein it comprises, as active principle, one or more β-(1,3)-glucuronans of formula (II):

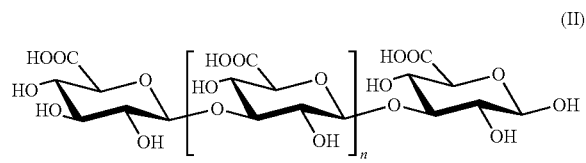

(II)

in which n is selected in such a way that the average molecular weights are between 500 and 2 500 000 dalton.

7. The composition as claimed in claim 1, wherein the compounds of formula (I) possess different degrees of oxidation and are selected from:
β-(1,3)-D-polyglucuronic acid having molecular weights between 500 and 2 500 000 dalton;
peracetylated β-(1,3)-D-polyglucuronic acid having molecular weights between 600 and 3 500 000 dalton; and
β-(1,3)-D-polyglucuronic acid, sulfated in positions C2 and C4 and having molecular weights between 800 and 4 000 000 dalton.

* * * * *